United States Patent [19]

Smith

[11] 4,272,505

[45] Jun. 9, 1981

[54] COMPETITIVE BINDING ANALYSIS BY FLUORESCENCE

[75] Inventor: David S. Smith, London, England

[73] Assignee: Technicon Instruments Corporation, Tarrytown, N.Y.

[21] Appl. No.: 830,009

[22] Filed: Sep. 1, 1977

[30] Foreign Application Priority Data

Aug. 17, 1976 [GB] United Kingdom ............... 38710/76

[51] Int. Cl.³ .................... G01N 33/78; G01N 33/58; G01N 33/54; G01N 21/64
[52] U.S. Cl. ...................................... 424/8; 23/230 B; 250/302; 424/1; 424/11; 424/12; 424/13
[58] Field of Search ..................... 424/1, 8, 11, 12, 13; 250/302; 23/230 R, 230 B; 435/7

[56] References Cited

U.S. PATENT DOCUMENTS

| | | | |
|---|---|---|---|
| 3,901,654 | 8/1975 | Gross | 424/8 X |
| 3,940,475 | 2/1976 | Gross | 424/8 X |
| 3,973,129 | 8/1976 | Blumberg | 250/461 B |
| 3,992,631 | 11/1976 | Harte | 424/12 X |
| 4,061,466 | 12/1977 | Sjoholm | 424/12 X |

OTHER PUBLICATIONS

Nilsson et al., J. Biol. Chem., vol. 250, No. 21, Nov. 1975, pp. 8554–8563.
Williams et al., Methods in Immunol. & Immuno-Chem. Acadamic Press, NY, vol. III, 1971, pp. 427–443.
Technicon, 1972 Technicon Int. Cong., Advances in Automated Analysis, vol. 4, 1973, pp. 87–91.

*Primary Examiner*—Anna P. Fagelson
*Attorney, Agent, or Firm*—S. P. Tedesco

[57] ABSTRACT

Thyroid hormones such as thyroxine and triiodothyronine are assayed in biological fluid samples by a competitive binding analysis in which a fluorescent label is used. Upon formation of complexes, the fluorescence of the labelled compound is released, and the hormone can be assayed by measuring the fluorescence of the mixture and comparing the result with standard data. Fluorescein is the preferred label. The process can be operated in a continuous flow manner.

6 Claims, 3 Drawing Figures

COMPETITIVE BINDING ANALYSIS BY FLUORESCENCE

This invention relates to a method of assaying biological fluids for thyroid hormones.

Disorders of thyroid function are among the commonest endocrine abnormalities encountered in clinical practice, and assays for thyroid hormones, e.g. thyroxine ($T_4$) and triiodothyronine ($T_3$) are frequently required. These assays are generally effected by the so-called competitive protein binding technique. In this technique, a mixture is formed of the sample (containing the thyroid hormone under assay), an amount of labelled thyroid hormone, and an antibody or other binding protein which will equilibrate with the labelled and unlabelled thyroid hormone to form complexes therewith:

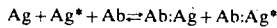

(where "Ag" is the unlabelled thyroid hormone under assay, "Ag*" is the labelled thyroid hormone and "Ab" is the binding protein). By measuring the labelled Ag* present either in the complex (bound fraction) or free fraction in solution (i.e. uncomplexed), it is possible to calculate the amount of thyroid hormone present in the original serum sample.

The label is a radioactive isotope, usually $^{125}I$, and whilst assays of this type are reasonably reliable and sensitive, they do have a number of disadvantages. Firstly, there are disadvantages in the use of radioactive labels in that they have a relatively short shelf life, they are hazardous to health and they necessitate the use of complex and expensive apparatus. Secondly, in the assay procedure described above, it is usually necessary to separate the complex from the mixture in order to measure how much of the labelled Ag* is present either in the complexed state or free in solution. The necessity for this separation step itself gives rise to a number of difficulties, three of the most important being as follows: Firstly, the separation step can be far from easy to effect satisfactorily. Secondly, it can be difficult to automate an assay procedure which involves a separation step, and this can make it difficult for such analyses to be effected by continuous flow techniques. Thirdly, and less importantly, it is in fact impossible using certain commonly applied techniques to carry out the separation step without disturbing the equilibrium to some extent, and when the association constant of the complex is low this may significantly reduce the reliability of the results.

Whilst it is possible to assay thyroid hormones by techniques different from that outlined above, these techniques are in the main inferior and less attractive. For example, they may be much more time-consuming and labor-intensive. For these reasons, the radioactive label technique is the one generally used despite its own drawbacks.

We have now devised another method of assaying biological fluids for thyroid hormones. In particular, we have found that when in the above-described competitive protein binding assay, certain fluorophores are used as labels in place of the radioactive label, the fluorophore exhibits a change in fluorescence when the fluorophore-labelled thyroid hormone binds to the binding protein to form a complex therewith. In particular, the fluorescence of the fluorophore is released, and as a result it is possible to assay a sample for thyroid hormone without the necessity for a separation step, i.e. without separating the complexes from the reaction mixture.

According to the invention, therefore, there is provided a method of assaying a biological fluid sample for a thyroid hormone, which comprises the steps of (1) forming a mixture of the sample with
  (a) a known amount of a covalent conjugate by labelling a thyroid hormone with a fluorophore, said fluorophore having a fluorescent level which is substantially suppressed by said thyroid hormone in said conjugate;
  (b) releasing the fluorescent level of the suppressed fluorophore of said conjugate by introducing into said mixture a binding substance which will equilibrate with both the thyroid hormone in said conjugate and said fluid sample, said binding substance sterically hindering the thyroid hormone of said conjugate from suppressing the fluorescence of said fluorophore such that the fluorescent level of said fluorophore is released;
  (c) measuring the fluorescence level of the mixture so formed; and
  (d) calculating the amount of thyroid hormone in the sample from the said fluorescence measurement and from standard data;

In a particular preferred embodiment, the invention provides a method of assaying a biological fluid sample for thyroxine which comprises the steps of:
  (1) forming a mixture of the sample with
    (a) a known amount of fluorescein-labelled thyroxine; and
    (b) anti-thyroxine antiserum;
  (2) measuring the fluorescence of the mixture so formed; and
  (3) calculating the amount of thyroxine in the sample from the fluorescence measurement as compared with standard fluorescent data.

The binding substance used in the method of the invention may be any binding protein (such as antibody) which will bind with both the thyroid hormone under assay and with the labelled conjugate XF.

The labelled substance XF is one which will equilibrate with the binding substance to form a complex. Substance X may itself be the thyroid hormone under assay and this is the more usual and generally preferred situation. However, substance X need not be identical to the hormone under assay but can be of slightly different structure, provided that it will complex with the binding substance. Thus, where it is difficult to attach a fluorescent label to a thyroid hormone itself, use may be made of a compound X which is structurally similar to the hormone but to which a label can more easily be attached.

As the label F, we prefer to use fluorescein but other substances may be used such as rhodamine, dansyl, fluorescamine, pyrene and 2-methoxy-2,4-diphenyl-3(2H)-furanone (MDPF).

When in the method of the invention, the mixture is formed in step (1), labelled conjugate XF binds to the binding substance to form a complex whose fluorescence is greater than that of the conjugate alone. Thus, the fluorescence of the mixture is released. In the case of an assay of $T_4$, using a conjugate of $T_4$ and fluorescein, the release of suppressed fluorescence upon formation of the complex is, we believe due to a steric hindrance effect. Thus, the binding of antibody to the $T_4$ moiety of the labelled $T_4$ sterically hinders the suppressing effect of the $T_4$ moiety on the fluorescence of the fluorescein moiety, resulting in release of suppressed fluorescence.

In the method of the invention, the fluorescence of the reaction mixture formed in step (1) is measured in step (2). (It will be understood that the fluorescence of the whole reaction mixture will include not only the fluorescence of the fluorophore but also any background fluorescence due to the other materials present. Allowance has to be made for this background fluorescence as will be appreciated by those skilled in the art.) By comparing the result with standard fluorescent data, for example a standard curve, the amount of thyroid hormone present in the sample under assay can be calculated. The standard curve for any particular system may be obtained as follows. Solutions of known concentration of the thyroid hormone are made up in a suitable buffer. To each of these is added a constant amount of fluorescent-labelled conjugate (XF) and sufficient binding substance to form a solution with a predetermined dilution of binding substance. The fluorescence intensities of the solutions are then measured and a standard curve of fluorescence intensity against the concentration of unlabelled thyroid hormone is plotted. Such a curve is then used to determine the amount of (unlabelled) thyroid hormone in a test sample, as follows. To a known volume of the sample (buffered if necessary) is added the said constant amount of labelled substance (XF) and an amount of binding substance sufficient to provide the dilution thereof used in the standard curve determination. The fluorescence intensity of the resulting mixture is measured and from the standard curve, the amount of thyroid hormone present can be determined.

As is well known in the immunoassay art, serum may contain proteins which can bind non-specifically with, for example, Ag (in this case thyroid hormones) and lead to a false result. When this occurs or is likely to occur, it is necessary to remove or inactivate these serum binding proteins prior to the assay. For example, in assaying human sera for $T_4$, it is necessary first to treat the serum to remove or inactivate the serum proteins. This can be effected in several ways as is well known in the art. It is to be understood, therefore, that the method of the invention includes the preliminary step, where necessary, of removing or inactivating serum proteins which might interfere with the assay.

The method of the invention can be effected in a continuous flow manner, wherein segments of the mixture formed in step (1) are flowed along a conduit, separated by segments of an inert fluid, and the fluorescence of the mixture segments is measured without any step of separation of reaction product from the mixture. Such a method can be carried out in an automated apparatus which comprises one or more mixing means for forming a mixture of the sample under test with a known quantity of the labelled conjugate XF and with the binding substance, means for passing said mixture through a fluorimeter for measurement of the fluorescence intensity thereof without any preliminary separation from the mixture of free or complexed labelled conjugate (XF), and means for recording the said measurement.

In order that the invention may be more fully understood, the following Examples are given by way of illustration only. In the Examples, reference is made to the accompanying drawings in which.

EXAMPLE 1: Preparation of fluorescein-labelled $T_4$ (hereinafter "FTC-$T_4$")

Solutions (20 mg/ml) of L-thyroxine (free acid) and fluorescein isothiocyanate (FITC) were made in a pyridine/water/triethylamine solvent of composition 9:1.5:0.1 V/V. To 1 ml of the $T_4$ solution was added 0.5 ml of the FITC solution, giving equimolar amounts of the reagents. This reaction mixture was left for one hour in the dark at room temperature. Then 10 ml of 0.2 M ammonium acetate, adjusted to pH 4.0 with acetic acid, was slowly added with constant mixing to precipitate the FTC-$T_4$ product. After centrifuging (MSE Multex, 3 min., 2,000 rpm) the supernatant was discarded and the precipitate resuspended briefly in 10 ml distilled water, then again spun down. This washed precipitate was dissolved in 4 ml 0.05 M ammonium bicarbonate (pH approximately 9). The solution was applied to a small (1×5 cm) column of Sephadex G-25 fine grade in 0.05 M ammonium bicarbonate. The FTC-$T_4$ became adsorbed to the Sephadex and small amounts of fluorescent impurities were removed by passing 40 ml of 0.05 M ammonium bicarbonate through the column. The FTC-$T_4$ product was then eluted from the Sephadex with distilled water (approximately 10 ml).

The FTC-$T_4$ product was shown to be pure by the criterion of paper chromatography on Whatman No. 1 paper, using MeOH/0.2 M $Na_2HPO_4$ 1:2 V/V as developing solvent. The product was stored frozen ($-18°$ C.), and has been found to be stable under these conditions for at least 15 months.

A repetition of the above synthesis using a $T_4$ solution to which a tracer amount of radioactive ($^{125}I$) $T_4$ had been added enabled determination of the extinction coefficient of FTC-$T_4$ at the fluorescein group absorption maximum in 0.075 M barbital buffer, pH 8.6, as $4.3 \times 10^4$ 1 mole$^{-1}$ cm$^{-1}$. Concentrations of FTC-$T_4$ quoted below are based on this estimation.

EXAMPLE 2: Antibody Dilution Curve

Figure 1:
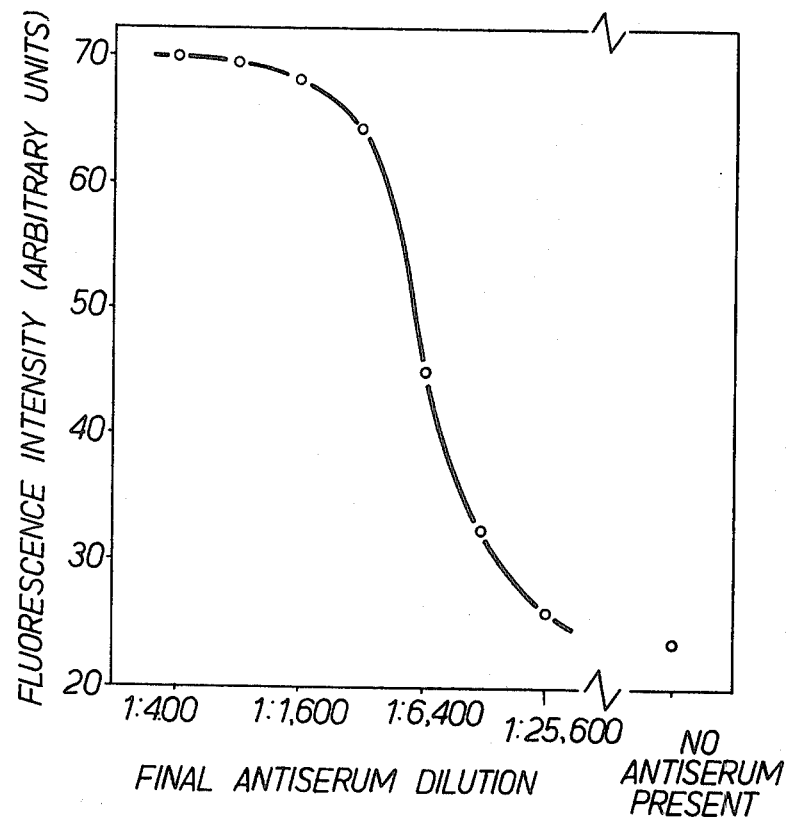
FIG. 1 is a graph of fluorescence intensities of mixtures of fluorescein-labelled $T_4$ and anti-$T_4$ serum plotted against varying anti-$T_4$ contents of the mixtures.

FTC-$T_4$ in 0.075 M barbital buffer, pH 8.6, was added to doubling dilutions of sheep anti-$T_4$ serum, prepared in the same buffer, so as to give a final concentration of FTC-$T_4$ of 9.3 nM. After a 15 min. incubation period to allow for equilibration, the total fluorescence intensity of each mixture was measured. The fluorescence background signal of the various final dilutions of anti-serum was separately measured in the absence of FTC-$T_4$ and, after correcting for this contribution to the total fluorescence intensity, the results shown in FIG. 1 were obtained. The results show that when the FTC-$T_4$ conjugate is bound by antibody, the fluorescence intensity of the complex is approximately three times that of the conjugate alone.

From the antibody dilution curve, a final anti-serum dilution of 1:3,000 was chosen for construction of a standard assay curve.

EXAMPLE 3: Standard Curve

Figure 2:
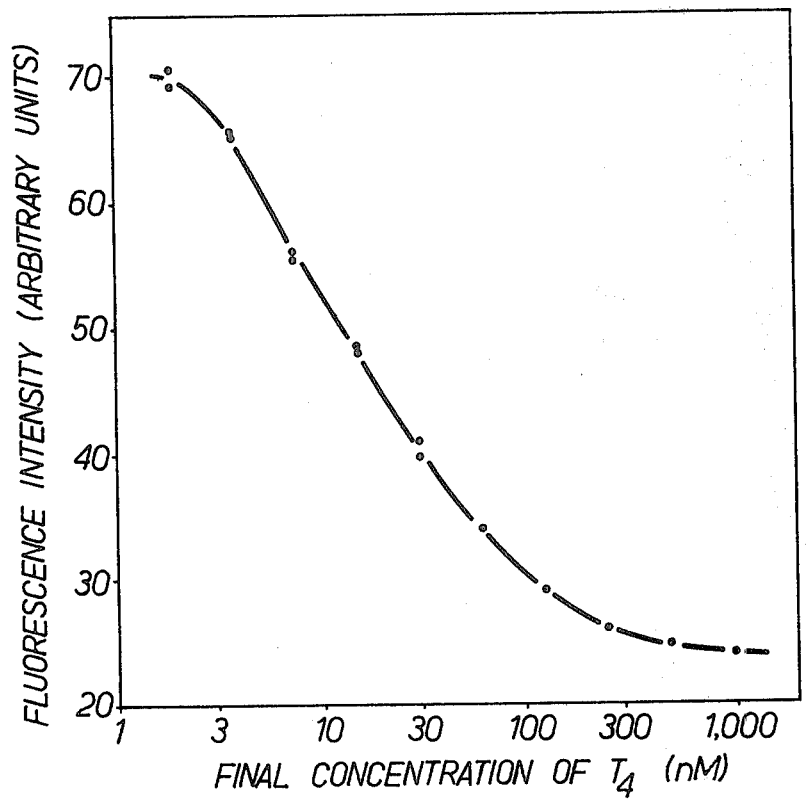
FIG. 2 is a standard curve for the fluorescein-labelled $T_4$/sheep anti-$T_4$ serum system.

Known concentrations of $T_4$ (unlabelled) were prepared in barbital buffer, and aliquots added to the same amount of FTC-$T_4$ as used in the construction of the antibody dilution curve. Then anti-$T_4$ serum was added to give a final dilution of 1:3,000. After 15 min. incubation time, the total fluorescence intensity of each assay mixture was measured. The background fluorescence signal of the antiserum alone at 1:3,000 dilution was recorded and subtracted from the total fluorescence intensity of each assay mixture to give the standard curve shown in FIG. 2.

EXAMPLE 4: Continuous-flow System for Automated Assay of $T_4$

Figure 3:
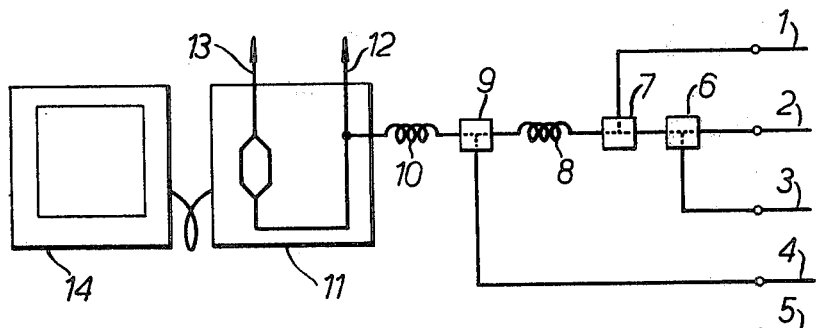
FIG. 3 shows schematically one arrangement of apparatus for carrying out the method of the invention in a continuous flow manner.

FIG. 3 of the accompanying drawings shows one form of flow system, suitable for a continuous-flow analysis. The system comprises sample input line 1, FTC-$T_4$ input line 2, air input line 3 and antiserum input line 4. Lines 2 and 3 meet at a segmenter 6 which is connected to junction 7 where line 1 joins line 2. Downstream of junction 7 line 2 is provided with a mixing coil 8 and then passes to junction 9 where line 4 joins. Downstream of 9 is a mixing coil 10 and finally a fluorimeter 11 having a waste outlet 12 and an outlet 13 downstream of the fluorescence cell connected to line 5 and thence to waste. the fluorimeter 11 is operatively coupled to recorder 14.

In operation, a controlled amount of FTC-$T_4$ enters line 2 and is segmented by air in segmenter 6. The sample to be tested (e.g. serum), treated and diluted as necessary, is introduced into the segmented stream in junction 7, followed by mixing in coil 8, then a controlled amount of antiserum is introduced in junction 9, followed by mixing in coil 10 before passing to fluorimeter 11.

What is claimed is:

1. A method of assaying a biological fluid sample for a thyroid hormone, comprising the steps of:
    (a) forming a mixture of said fluid sample with a known amount of conjugate formed by labeling a thyroid hormone with a fluorophore, said fluorophore having a fluorescent level which is substantially suppressed by said thyroid hormone in said conjugate;
    introducing into said mixture a binding substance which will equilibrate with both the thyroid hormone in said conjugate and said fluid sample, said binding substance sterically hindering the thyroid hormone of said conjugate from suppressing the fluorescence of said fluorophore;
    (c) measuring the fluorescent level of said mixture; and
    (d) calculating the amount of thyroid hormone in said sample by comparing the fluorescent level of said mixture with a standard fluorescent level.

2. A method according to claim 1 wherein the biological fluid sample contains a thyroid hormone selected from a group consisting of thyroxine and triodothyronine.

3. A method according to claim 1, wherein the fluorophore from which the said conjugate has been formed is fluorescein.

4. A method according to claim 1, wherein the fluorophore from which the said conjugate has been formed is selected from a group consisting of: dansyl, rhodamine, fluorescamine, pyrene and 2-methoxy-2,4-dyphenyl-3(2H)-furanone.

5. A method of assaying a biological fluid sample for thyroxine which comprises the steps of: (1) forming a mixture of a sample containing an unknown amount of thyroxine with
    (a) a known amount of fluorescein-labelled thyroxine; and
    (b) anti-thyroxine antiserum; (2) measuring the fluorescence of the mixture so formed; and (3) calculating the amount of thyroxine contained in the sample from the fluorescence measurement as compared with standard fluorescent data.

6. A method of assaying a sample fluid for a thyroid hormone, which contains iodine, comprising
    (a) forming a mixture of said sample with a known amount of a conjugate formed by labeling said thyroid hormone with a fluorophore;
    (b) adding to said mixture a known amount of a binding substance for said thyroid hormone, said binding substance hindering the fluorescence inhibiting action of the iodine contained in said thyroid hormone;
    (c) measuring the fluorescent level of the mixture;
    (d) calculating the amount of thyroid hormone in said sample by comparing the fluorescent level with that of a standard.

* * * * *